(12) United States Patent
Hall et al.

(10) Patent No.: US 7,666,153 B2
(45) Date of Patent: *__Feb. 23, 2010__

(54) CPR COMPRESSION DEVICE AND METHOD INCLUDING A FLUID FILLED BLADDER

(75) Inventors: Gregory W. Hall, Sunnyvale, CA (US);
James O. Jensen, Sunnyvale, CA (US);
Paul Escudero, Sunnyvale, CA (US);
Darren R. Sherman, Sunnyvale, CA (US); Bob Katz, Sunnyvale, CA (US)

(73) Assignee: Zoll Circulation, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/221,092

(22) Filed: Sep. 6, 2005

(65) Prior Publication Data
US 2006/0009717 A1    Jan. 12, 2006

Related U.S. Application Data

(63) Continuation of application No. 10/192,771, filed on Jul. 10, 2002, now Pat. No. 6,939,314, which is a continuation-in-part of application No. 09/866,377, filed on May 25, 2001, now Pat. No. 6,616,620.

(51) Int. Cl.
*A61H 31/00* (2006.01)

(52) U.S. Cl. .................................. 601/41; 601/DIG. 7

(58) Field of Classification Search ............ 601/41–44, 601/DIG. 7, 148–152
See application file for complete search history.

(56) References Cited

U.S. PATENT DOCUMENTS

| | | | |
|---|---|---|---|
| 443,204 A | 12/1890 | Davis | |
| 651,962 A | 6/1900 | Boghean | 501/41 |
| 2,071,215 A | 2/1937 | Petersen | 128/28 |
| 2,486,667 A | 11/1949 | Meister | 128/28 |
| 2,699,163 A | 1/1955 | Engstrom | 128/29 |
| 2,754,817 A | 7/1956 | Nemeth | 128/60 |
| 2,853,998 A | 9/1958 | Emerson | 128/30 |
| 2,899,955 A | 8/1959 | Huxley, III et al. | 128/30 |
| 3,042,024 A | 7/1962 | Mendelson | 128/30 |
| 3,120,228 A | 2/1964 | Huxley, III | 128/30 |
| 3,368,550 A | 2/1968 | Glascock | 128/2 |
| 3,461,860 A | 8/1969 | Barkalow et al. | 128/53 |
| 3,481,327 A | 12/1969 | Drennen | 128/30.2 |
| 3,503,388 A | 3/1970 | Cook | 128/28 |
| 3,777,744 A | 12/1973 | Fryfogle | 128/28 |
| 3,782,371 A | 1/1974 | Dorouineau | 128/28 |
| 4,004,579 A | 1/1977 | Dedo | 128/28 |
| 4,338,924 A | 7/1982 | Bloom | 128/28 |

(Continued)

FOREIGN PATENT DOCUMENTS

JP    8052217    2/1996

(Continued)

*Primary Examiner*—Danton DeMille
(74) *Attorney, Agent, or Firm*—K. David Crockett, Esq.; Crockett & Crockett

(57) ABSTRACT

Improved automatic chest compression systems which use constricting belts, repeatedly inflating bladders, or reciprocating pistons to compress the chest. A bladder is placed between the chest and the particular mechanism used to compress the chest during CPR. The bladder maximizes the effectiveness of chest compressions.

27 Claims, 9 Drawing Sheets

U.S. PATENT DOCUMENTS

| | | | |
|---|---|---|---|
| 4,349,015 A | 9/1982 | Alferness | 128/28 |
| 4,397,306 A | 8/1983 | Weisfeldt et al. | 128/28 |
| 4,570,615 A | 2/1986 | Barkalow | 128/28 |
| 4,628,945 A | 12/1986 | Johnson, Jr. et al. | 602/27 |
| 4,664,098 A | 5/1987 | Woudenberg et al. | 128/53 |
| 4,770,164 A | 9/1988 | Lach et al. | 128/28 |
| 4,915,095 A | 4/1990 | Chun | 128/28 |
| 4,928,674 A | 5/1990 | Halperin et al. | 128/30.2 |
| 5,056,505 A | 10/1991 | Warwick et al. | 128/30.2 |
| 5,098,369 A | 3/1992 | Heilman et al. | 600/16 |
| 5,184,606 A | 2/1993 | Csorba | 128/28 |
| 5,217,010 A | 6/1993 | Tsitlik et al. | 128/419 PG |
| 5,222,478 A | 6/1993 | Scarberry et al. | 128/30.2 |
| 5,257,619 A | 11/1993 | Everete | 128/28 |
| 5,277,194 A | 1/1994 | Hosterman et al. | 128/721 |
| 5,287,846 A | 2/1994 | Capjon et al. | 128/28 |
| 5,295,481 A | 3/1994 | Geeham | 601/43 |
| 5,327,887 A | 7/1994 | Nowakowski | 128/204.21 |
| 5,359,999 A | 11/1994 | Kinsman | 128/204.21 |
| 5,370,603 A | 12/1994 | Newman | 601/41 |
| 5,372,487 A | 12/1994 | Pekar | 417/480 |
| 5,399,148 A | 3/1995 | Waide et al. | 601/41 |
| 5,405,362 A | 4/1995 | Kramer | 607/5 |
| 5,474,533 A | 12/1995 | Ward et al. | 604/26 |
| 5,490,820 A | 2/1996 | Schock et al. | 601/41 |
| 5,577,998 A | 11/1996 | Johnson, Jr. et al. | 602/5 |
| 5,630,789 A | 5/1997 | Schock et al. | 601/41 |
| 5,664,563 A | 9/1997 | Schroeder et al. | 128/204.25 |
| 5,738,089 A * | 4/1998 | Hoshi et al. | 128/204.18 |
| 5,738,637 A | 4/1998 | Kelly et al. | 601/41 |
| 5,743,864 A | 4/1998 | Baldwin et al. | 601/41 |
| 5,769,800 A | 6/1998 | Gelfand et al. | 601/151 |
| 6,066,106 A | 5/2000 | Sherman et al. | 601/41 |
| 6,090,056 A | 7/2000 | Bystrom et al. | 601/41 |
| 6,142,962 A | 11/2000 | Mollenauer et al. | |

FOREIGN PATENT DOCUMENTS

| | | |
|---|---|---|
| WO | WO 9628129 A1 * | 9/1996 |
| WO | WO 97/22327 | 6/1997 |
| WO | WO 0027334 A2 * | 5/2000 |
| WO | WO0027336 | 5/2000 |

* cited by examiner

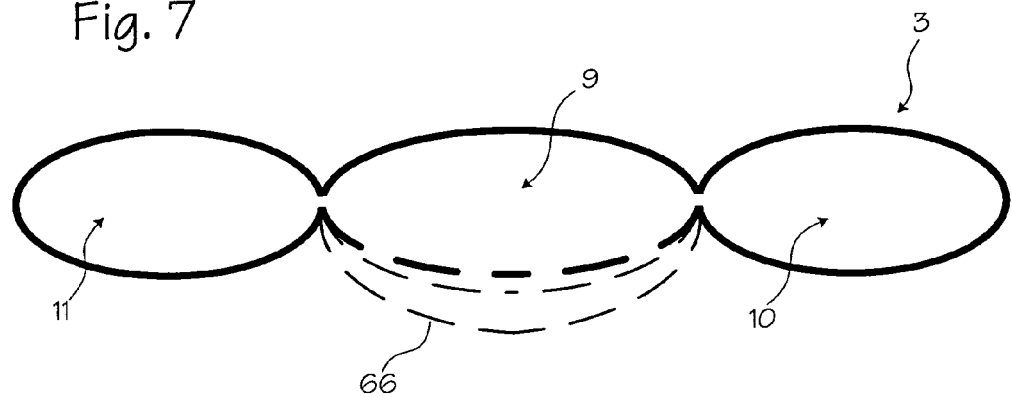
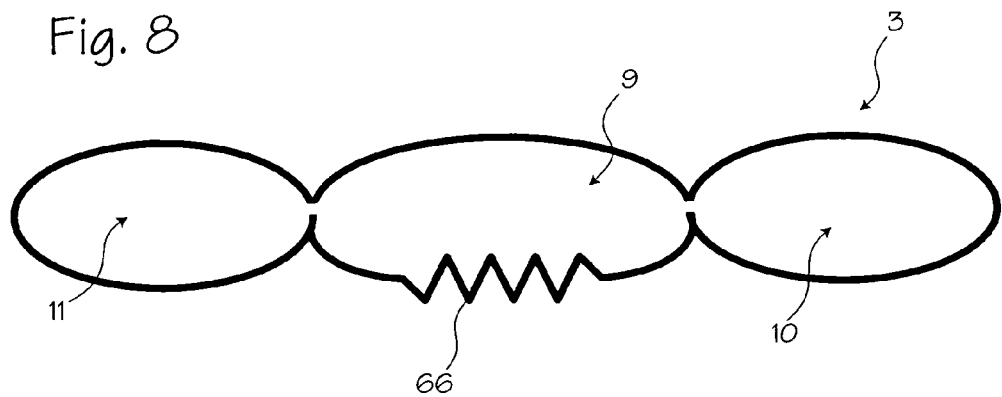

CPR COMPRESSION DEVICE AND METHOD INCLUDING A FLUID FILLED BLADDER

This application is a continuation of U.S. application. Ser. No. 10/192,771 filed Jul. 10, 2002, now U.S. Pat. No. 6,939,314, which is a continuation-in-part of application Ser. No. 09/866,377, filed May 25, 2001 now U.S. Pat. No. 6,616,620.

FIELD OF THE INVENTION

This invention relates to emergency medical devices and methods and the resuscitation of cardiac arrest patients.

BACKGROUND OF THE INVENTION

Current American Heart Association guidelines call for chest compressions during cardio-pulmonary resuscitation (CPR) to be performed at a rate of 80 to 100 per minute and at a depth of 1.5 inches to 2.0 inches. (Guidelines 2000 for Cardiopulmonary Resuscitation and Emergency Cardiovascular Care, 102 Circulation Supp. I (2000).) When a first aid provider performs CPR according to these guidelines, blood flow in the body is about 25 to 30% of normal. However, when chest compressions are required for long periods of time it is difficult, if not impossible, to maintain adequate compression of the heart and rib cage. Even experienced paramedics cannot maintain adequate chest compressions for more than a few minutes. Hightower, et al., Decay In Quality Of Chest Compressions Over Time, 26 Ann. Emerg. Med. 300 (September 1995). Thus, long periods of CPR, when required, are often not successful at sustaining or reviving the patient. At the same time, it appears that if chest compressions could be adequately maintained then cardiac arrest victims could be sustained for extended periods of time. Occasional reports of extended CPR efforts (45 to 90 minutes) have been reported, with the victims eventually being saved by coronary bypass surgery. See Tovar, et al., Successful Myocardial Revascularization and Neurologic Recovery, 22 Texas Heart J. 271 (1995).

In efforts to provide better blood flow and increase the effectiveness of resuscitation efforts, we have developed a chest compression system which automatically compresses the chest of a heart attack victim. The device includes a broad belt that wraps around the chest of the patient. The belt is repeatedly tightened around the chest to cause the chest compressions necessary for CPR. Our devices are described in co-pending application Ser. No. 09/866,377 filed May 21, 2001 and Ser. No. 09/087,29 filed May 29, 1998, the entire disclosures of which are hereby incorporated by reference. Other modifications of the basic CPR procedure have been proposed. Woudenberg, Cardiopulmonary Resuscitator, U.S. Pat. No. 4,664,098 (May 12, 1987) shows such a chest compression device that is powered with an air cylinder. Waide, et al., External Cardiac Massage Device, U.S. Pat. No. 5,399,148 (Mar. 21, 1995) shows another such device which is manually operated. Lach, et al., Resuscitation Method and Apparatus, U.S. Pat. No. 4,770,164 (Sep. 13, 1988), proposed compression of the chest with wide band and chocks on either side of the back, applying a side-to-side clasping action on the chest to compress the chest. Kelly et al., Chest Compression Apparatus for Cardiac Arrest, U.S. Pat. No. 5,738,637 (Apr. 14, 1998) uses a flexible, inelastic belt attached to a scissors-like means for compressing the chest. Inflatable vests are also proposed for compressing the chest for CPR, as shown in Halperin, Cardiopulmonary Resuscitation and Assisted Circulation System, U.S. Pat. No. 4,928,674 (May 29, 1990). The commercially available Thumper device, shown in Barkolow, Cardiopulmonary Resuscitator Massager Pad, U.S. Pat. No. 4,570,615 (Feb. 18, 1986) and other such devices, provides continuous automatic closed chest compression. Barkolow provides a piston which is placed over the chest cavity and supported by an arrangement of beams. The piston is placed over the sternum of a patient and set to repeatedly push downward on the chest under pneumatic power.

SUMMARY

The devices and methods described below provide for improved chest compression in automatic chest compression systems which use constricting belts, repeatedly inflating bladders, or reciprocating pistons to compress the chest. A bladder is placed between the chest and the particular mechanism used to compress the chest during CPR. The bladder maximizes the effectiveness of chest compressions in a wide class of patients. The bladder also helps to ensure that unequal or unnecessary pressure is not applied to the rest of the thorax, and evenly distributes the pressure applied by the belt, bladder, or piston used for compression.

The bladder may be provided in several forms. The bladder may be constructed with three or more laterally arranged chambers or sections in fluid communication with each other. The bladder may be filled with a resilient reticulated or open cell foam to provide structural resilience to the bladder. An equalizing valve may be provided in the bladder to allow the pressure in the bladder to equalize with ambient atmospheric pressure. Otherwise, the bladder is substantially fluid-tight, and does not permit substantial flow of fluid into and out of the bladder during compressions, in contract to active bladders used in inflatable vest systems.

BRIEF DESCRIPTION OF THE DRAWINGS

FIG. 7 illustrates a cross section of a bladder with the bottom surface of the central section made from an elastic material.

FIG. 8 illustrates a cross section of a bladder where the bottom surface of the central section is provided with pleats.

DETAILED DESCRIPTION OF THE INVENTION

Figure 1:
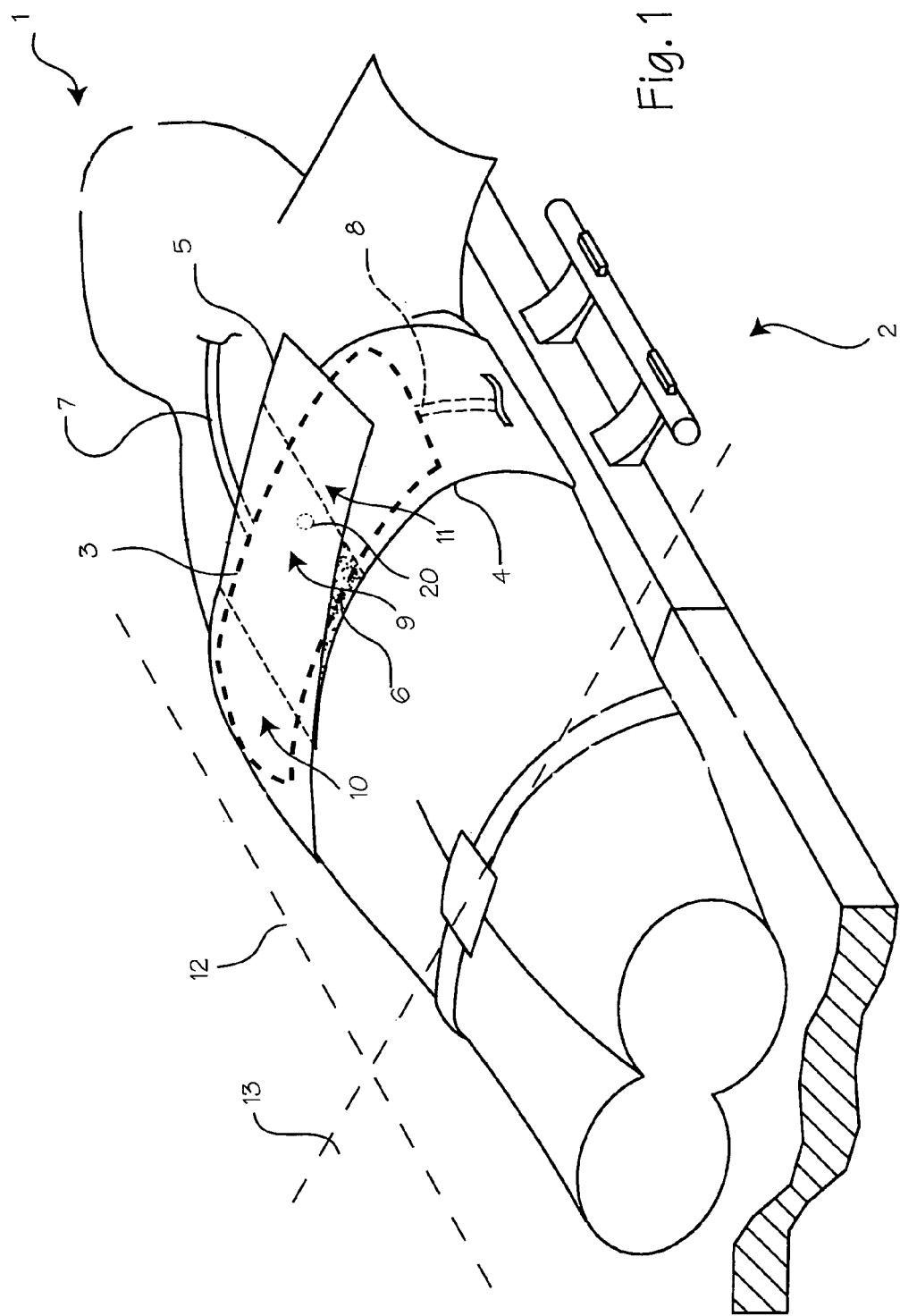
FIG. 1 illustrates a patient receiving chest compressions from a chest compression device in conjunction with a bladder.

FIG. 1 illustrates a patient 1 with a chest compression device 2 fitted on the patient and ready for use. A belt 3 and a belt tightening mechanism within the backboard comprises the means for compressing the chest of the patient. The belt is operably connected to the belt tightening mechanism, which provides the force necessary to tighten the belt about the patient's chest and thorax. The belt tightening mechanism may be a motor and motor driven spool as shown in co-pending application Ser. No. 09/866,377, other automatic means for tightening the belt, or a pull-lever or other manual means for tightening the belt.

A bladder 4 is disposed between the patients chest and the compression belt. The bladder 4, shown in phantom to indicate its position below the belt, is secured to the belt 3. In turn, the belt is secured to the body with two overlapping areas 5 and 6 of hook and loop fastener, Velcro®, or other fastener. The bladder 4 may be provided with a sensing line 7 which is connected to a pressure transducer or other means for measuring the pressure in the bladder. The pressure transducer is in turn electrically connected to a controller. The bladder itself may be provided with the pressure transducer, in which case a signal transmission cable 8 electrically connects the pressure transducer to a controller. The controller, as illustrated in co-pending application Ser. No. 09/866,377, uses the pressure in the bladder as feedback for controlling the force of compression and the amount of belt tightening accomplished by the belt tightening mechanism.

The central section 9 of the bladder 4 is disposed over the sternum of the patient. The right lateral section 10 is disposed over the right lateral portion of the patient's chest and the left lateral section 11 is disposed over the left lateral portion of the patient's chest. The left and right lateral sections of the bladder extend along the medial-lateral direction over the patient's rib cage. Depending on the length of the bladder, the left lateral and right lateral sections may completely cover the patient's rib cage. For most patients, however, the bladder covers the anterior surface of the chest from armpit to armpit and along the superior-inferior length of the sternum. Thus, the entire bladder 4 may be about 6 to 8 inches high (as defined by superior-inferior axis 12), about 12 to 16 inches wide (as defined by medial-lateral axis 13), and about 1.5 inches thick. When provided in this size range, the bladder will cover substantially the entire chest of a typical patient. Specifically, a rectangular bladder of about 8 inches high by about 16 inches wide (again, relative to the patient) by about 1.5 inches thick is suitable to fit most patients, and may be provided for use on all patients.

The bladder 4 is filled with a pressure-transmitting medium, such as a gas or liquid. The bladder may also be filled with foam, such as an open-cell foam or a filter foam, that allows air to flow throughout the bladder. The foam provides the bladder with structural support such that the bladder does not collapse if the bladder is not filled with a pressure-transmitting medium. In addition, the bladder 4 may be provided with a valve 20 that allows a user to either increase or decrease the pressure inside the bladder.

For most patients the sternum is easier to compress than the rest of the chest and thorax; thus, during compressions the bladder's right lateral section 10 and left lateral section 11 are compressed more than the central section 9. In response, the fluid in the bladder is forced into the bladder's central section. The central section will bulge in response to the pressure and the bulging results in preferential displacement of the sternum. This effect occurs in both single-sectioned and multi-sectioned bladders.

In all patients, the bladder alters the pressure on the patient's chest during compressions, creating a uniform field of pressure over the entire chest. The uniform pressure field has the effect of first compressing the chest in the most compliant regions of the chest. (Hence, in most patients the peri-sternal region is compressed first). In turn, the next most compliant part of the chest will be compressed somewhat more than the next least compliant portion. Ultimately, the entire chest is compressed to at least some extent, with the most compliant regions of the chest being compressed more than the least compliant regions of the chest. Thus, during chest compressions, the pressure field maximizes the reduction in thoracic volume for a given force applied to the chest. Accordingly, the presence of the bladder creates more effective blood circulation during chest compressions.

In addition, the bladder allows the chest compression device to apply more total force to the patient while also decreasing the probability of hurting the patient, since the force per unit area on the chest is altered by the presence of the bladder. A bladder allows the total force applied to the chest to be about 100 pounds to about 700 pounds. We preferably apply about 350 to 400 pounds of total force to the chest with the chest compression belt illustrated in the Figures. Thus, the bladder allows a chest compression device to far exceed previously known total force limits during chest compressions while maintaining or decreasing the probability, as compared to manual compressions or device-driven compressions without a bladder, of injuring the patient. Conversely, because the bladder may have a bottom surface area of about 100 square inches, the force density (the per square inch force applied) may be well below typical manual CPR levels, and effective CPR compressions can be provided with forces of less than 10 psi applied on the chest. We preferably apply about 2.50 to 4 pounds per square inch to chest with the chest compression belt illustrated in the Figures.

Figure 2:
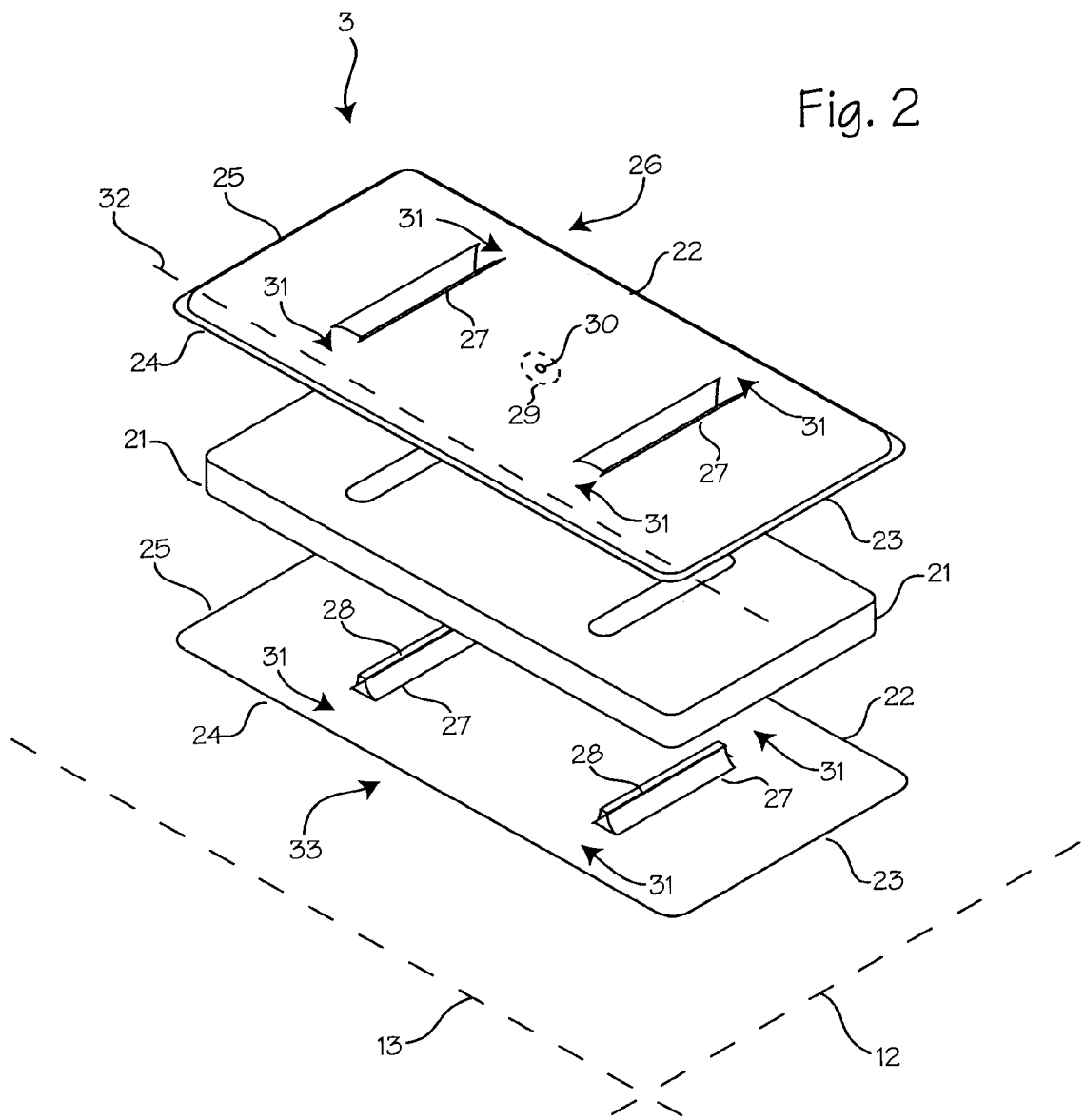
FIG. 2 illustrates an exploded view of the bladder.

FIG. 2 illustrates an exploded view of the bladder 4, including a foam insert 21. The bladder 4 is formed from two pieces of material melted, glued, or otherwise joined together along edges 22, 23, 24, and 25. In addition, the front side 26 and back side 33 of the bladder 4 are joined or sealed together (mechanically or otherwise) at two dividers 27, also referred to as dividing seams. Each divider 27 is about $\frac{1}{16}$ inch to about 1 inch wide (as defined by superior-inferior axis 12) and about ½ inch to about the length of the bladder long (as defined by lateral-medial axis 13). Furthermore, creases 28 may be placed in the dividers so that the bladder 4 more easily folds. An equalizing check valve 29 is placed in line with an aperture 30 to provide for equalization of the bladder pressure with ambient atmospheric pressure when the device is not in use, while providing a tight seal during compressions, as more fully explained below.

Preferably, each divider 27 does not completely seal off the individual sections from each other (the dividers do not extend along the entire superior-inferior height of the bladder). Thus, fluid can communicate between the sections through fluid communication channels 31. Nevertheless, in alternate embodiments the dividers may completely seal one or more bladder sections from the other bladder sections. In addition, the dividers 27 are disposed away from the center of the bladder such that the center section may be wider along medial-lateral axis 13 than the left lateral and right lateral sections. Thus, the central section is large enough to expand and effectively compress the sternum.

Figure 3:
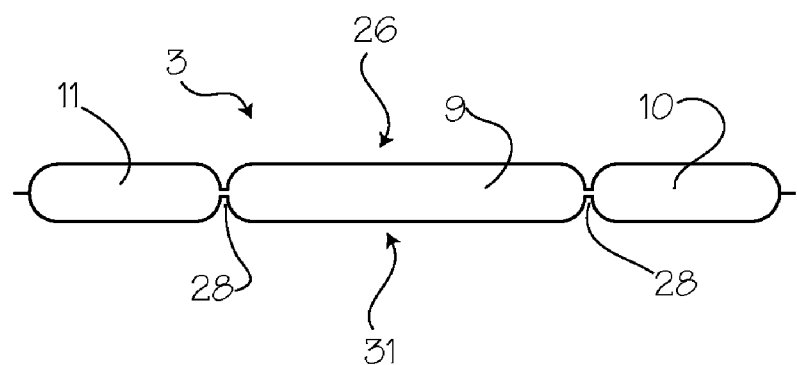
FIG. 3 illustrates a cross section of the bladder.

FIG. 3 illustrates a cross section of the bladder 4, showing the three bladder sections (the right lateral section 10, the left lateral section 11, and the center section 9). The cross section is taken along line 32 in FIG. 2 (which passes through the fluid communication channels 31). The front side 26 and the back side 33 of the bladder are not joined at the fluid communication channels 31; thus, fluid may pass between the bladder sections. The bladder illustrated has been formed of a single bladder with multiple chambers having fluid communication channels connecting the chambers. The bladder system may also be considered as several distinct bladders fastened together and connected by tubes which provide for the desired fluid communication between the bladders.

Figure 4:
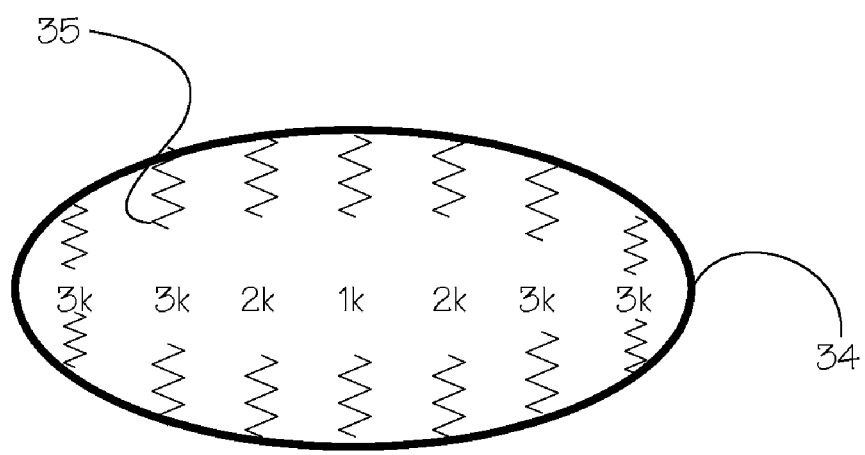
FIG. 4 illustrates the stiffness of a patient's thorax modeled as a series of springs.

FIG. 4 illustrates the stiffness of a hypothetical patient's thorax 34 modeled as a series of springs 35 of differing spring constants. For most patients, the area corresponding to the sternum is most compliant (least stiff) and thus is labeled as having a spring constant 1K. The lateral portions of the thorax are less compliant (more stiff) and thus are labeled as 2K or 3K. Since less force is needed to compress the sternal area of the thorax, energy efficiency is greatest when compressing the sternum. This effect increases as the chest is compressed further towards the spine. The addition of the bladder to the chest compression belt provides a compression device which takes advantage of this model, as shown in FIGS. 5 and 6.

Figure 5:
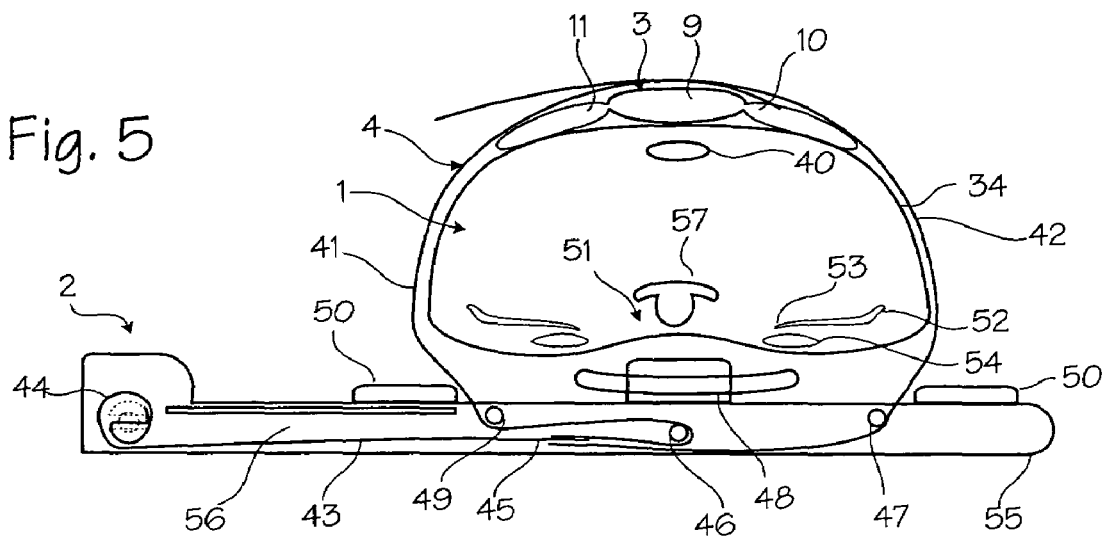
FIG. 5 is a cross section of a patient in an automatic chest compression device and a bladder disposed over the sternum of the patient.

FIG. 5 is a cross section of a patient 1 in an automatic chest compression device 2 with bladder 4 disposed over the sternum 40 of the patient, between the chest of the patient and the belt. The device is similar to that described in our parent patent application Ser. No. 09/866,377. The bladder 4, having a central section 9, a right lateral section 10, and left lateral section 11, is disposed over the patient's sternum. The bladder helps apply force preferentially to the sternum while ensuring that other areas of the thorax receive an even distribution of force during compressions.

The belt left section 41 and right sections 42 are joined in a seam to pull straps 43. The pull straps are fixed to the drive spool 44. The belt right section 42 extends from the pull strap medial end 45 (that is, the end near the medial area of the body, when applied to a patient), under the medially located lower spindle 46 and the lateral upper right spindle 47, under a spinal support platform 48 and further outward to extend under the right flank of the patient when in use. The belt left section 41 extends from the pull strap medial end 45, reversing direction around the lateral upper left spindle 49, under the spinal support platform 48 and further outward to extend under the left flank of the patient when in use. When not in use the belt is contained in belt housings 50. The spinal support platform 48 extends inferiorly and superiorly over the cartridge and serves to support the patient over the cartridge and away from the underlying area in which the belt runs into the cartridge. Thus a large portion of the frictional load that the belt would otherwise have to overcome during operation is eliminated. A PTFE (Teflon®) sheet (not shown) may be provided on the upper surface of the spinal support platform to reduce friction and rubbing due to chest compressions. Depending on the lateral spacing of the lateral spindles, the belt may engage the chest without engaging the side and back portion of the thorax, or it may engage substantially the entire circumference of the thorax. As shown, the lateral spindles are spaced so that the belt engaged the chest and sides of the patient, but does not directly engage the patient's back.

Figure 6:
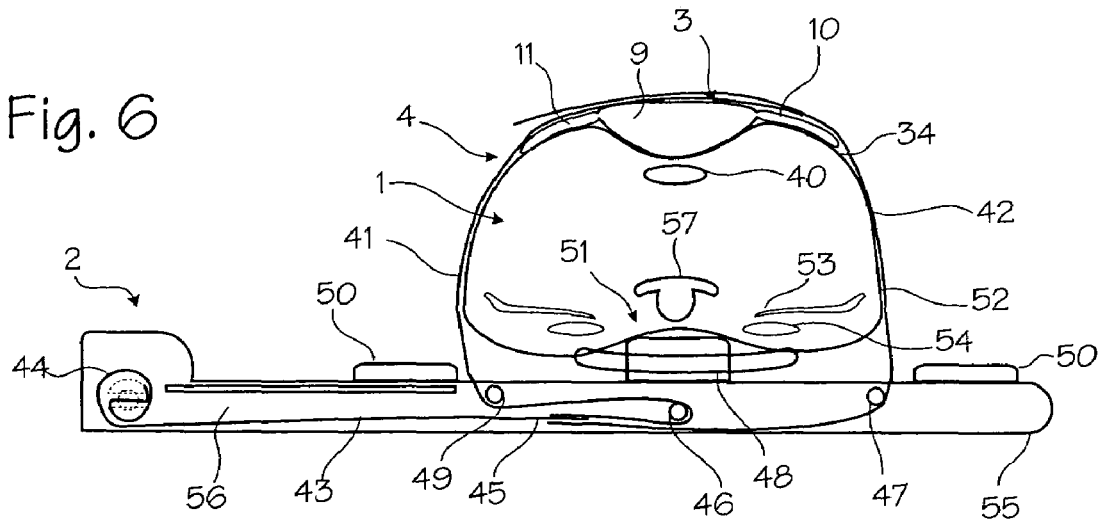
FIG. 6 is a cross section of a patient in an automatic chest compression device during a compression and a bladder disposed over the sternum of the patient.

The operation of the spinal support platform 48 can also be seen in FIGS. 5 and 6. The platform extends laterally across the spinal depression 51 that runs up and down the back. The width of the spinal support platform is chosen so that, in most patients, it extends laterally to the shoulder blades (scapula) 52 or medial border of the scapula 53 of the patient, or to the protrusion of the trapezius muscle 54 on either side of the spinal depression of the back 51. The platform thus spans the spinal depression 51, and extends bi-laterally across the spinal depression to the protrusions of the trapezius muscle 54 or the medial border of the shoulder blade 53. The belt sections 42 and 41 pass under the platform through a vertical gap between the platform and the cartridge or back plate, thereby avoiding running directly between the patient's body and the cartridge for a small lateral width extending slightly beyond the width of the platform. Also shown in FIGS. 5 and 6 are the right lateral support plate 55 and left lateral support plate 56 of the automatic chest compression device. The patient's thorax 34 and spine 57 are also shown for reference.

FIG. 6 is a cross section of a patient 1 disposed in an automatic chest compression device 2 during a compression and a bladder 4 disposed over the sternum 40 of the patient. During compressions the thorax 34 is maintained in a somewhat oval cross section. However, since the lateral portions of the thorax are less compressible than the sternum, the force of compressions forces fluid pressure from the left lateral section 11 and right lateral section 10 to the center section during compressions. In response, the center section 9 deforms preferentially, causing the sternum to compress more than if there had been no bladder.

As seen in FIGS. 5 and 6, the bladder has a first relaxed configuration which it assumes when the belt is loosened about the chest, as in FIG. 5, and a second pressurized configuration which it assumes when the belt is constricted about the chest of the patient, as in FIG. 6. In the relaxed configuration, the right lateral section, center section and left lateral section are each filled with fluid. In the pressurized configuration, the right lateral section and left lateral section are substantially compressed and some or all of the fluid therein is forced into the center section. (The bladder is substantially fluid-tight, and does not permit substantial flow of fluid into and out of the bladder during compressions.) The relative sizes of the bladder sections may be adjusted (by appropriate location of the seams that join the upper and lower sheets) to provide chambers of appropriate relative size so that the lateral chambers are not fully compressed and emptied of fluid when compressed with the forces expected during compressions, and the anterior-posterior bulging of the central section is limited. (In the case of a single sectioned bladder the sternum will still be preferentially compressed. The edges of the single-section bladder will still be squeezed, forcing fluid into the central portion of the bladder. Thus, the central portion of the single sectioned bladder expands and causes the thorax to compress preferentially.)

FIG. 7 illustrates a cross section of a bladder 4 with the bottom surface 66 of the central section made from an elastic material, such as latex. Alternatively, the bladder bottom surface 66 can be neoprene, rubber, rubber-coated lycra, or some other elastic material. Although only the bottom portion of the central section 9 is made from an elastic material, the entire central section can also be made from an elastic material. In contrast, the right lateral section 10 and left lateral section 11 are made from a relatively inelastic material. In the case of a single-sectioned bladder, a portion of the bottom surface may be made from an elastic material.

When the bladder comes under the expected load from a compression belt, the fluid in the lateral sections 10 and 11 will move into the central section 9. Since the bottom surface 66 of the central section is flexible, the central section 9 will expand more than when the central section does not have an elastic bottom surface. In the case of a single sectioned bladder, the lateral portions of the bladder will force fluid into the central portion of the bladder, causing the elastic portion to expand preferentially. The central portion of the bladder expands in the posterior direction relative to the patient, distributing the force applied by the belt evenly over compliant and non-compliant portions of the chest. In the typical patient, the sternum is displaced posteriorly with this device.

FIG. 8 illustrates a cross section of a bladder 4 where the bottom surface 66 of the central section 9 is provided with pleats or folds, which are oriented up and down relative to the body of the patient. The entire bladder is made from a relatively inelastic material, though the pleated section could be made from an elastic material. Alternatively, the entire central section 9 could be made such that both the top and bottom surfaces are pleated. In either case, the number of pleats or folds in the pleated bottom surface shown is within the range of 1 to about 10 pleats (2 to about 20 bends), though about 5 pleats (10 bends) is used for most patients. In the case of a single-sectioned bladder, a portion of the bottom surface may be pleated.

When the bladder experiences a load the lateral sections 10 and 11 will transfer pressure to the central section 9. Since the bottom surface 66 of the central section is pleated it will expand preferentially. In the case of a single sectioned bladder, the lateral sections of the bladder will force fluid into the central sections of the bladder, causing the pleated portion to expand preferentially. Since the central portion of the bladder expands preferentially, the sternum also compresses preferentially.

Figure 9:
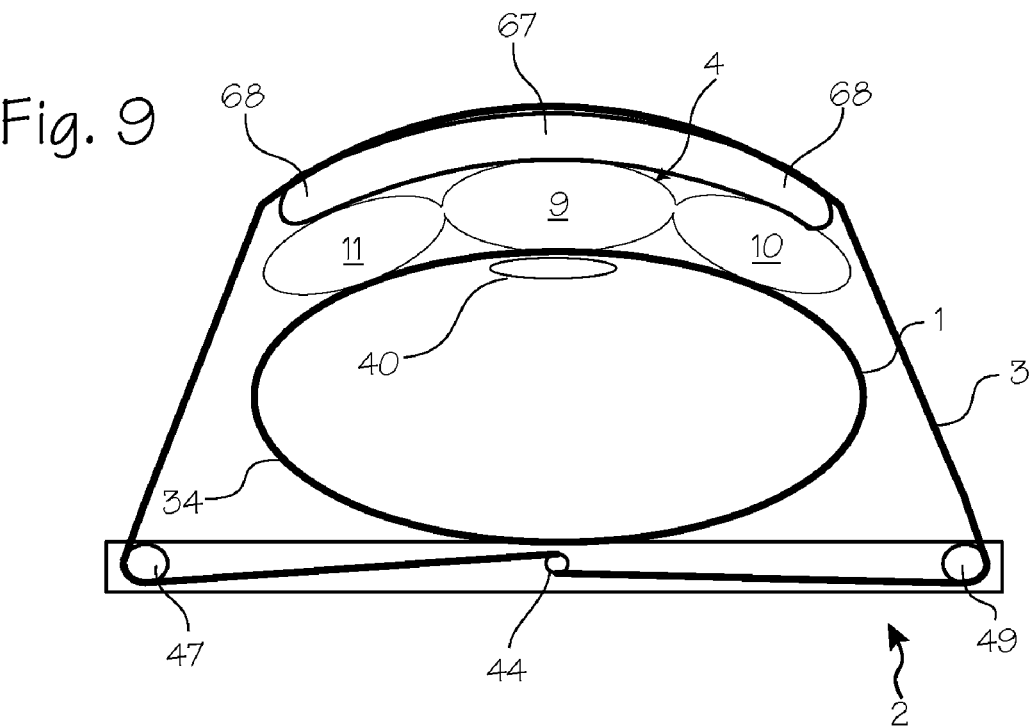
FIG. 9 illustrates a patient in an automatic chest compression device, a first bladder disposed above the sternum, and a second bladder disposed above the bladder.

FIG. 9 illustrates a patient 1 in an automatic chest compression device 2, a first bladder 4 disposed above the sternum, and a second bladder 67 disposed above the first bladder. (The second bladder may also be a pad, a single section of foam, or a multi-sectioned bladder). The belt in this Figure is spooled upon a centrally located drive spool 44, which spools the belt as it is drawn over the laterally located spindles 47 and 49. The spindles are laterally spaced wider than the patient's thorax 34, so that the belt extends over the chest without substantially engaging the remainder of the thorax. The belt 3, or other means for compressing the chest, secures both bladders to the patient's chest (the anterior surface of the thorax 34). The second bladder 67 is constructed with a relatively inelastic material such that its shape changes only slightly with changes in pressure. The second bladder may be filled with a pressure-transmitting medium such as air, gel, hydrogel, foam, water, or other suitable fluids.

The second bladder 67 alleviates local areas of high pressure on the patient's thorax 34. In other words, in areas other than over the sternum, the pressure will remain evenly distributed. During compressions, the second bladder also helps to transfer pressure from the lateral sections 68 of the second bladder to the central section 9 of the bladder by pressing on the lateral sections 10 and 11 of the bladder 4.

Figure 10:
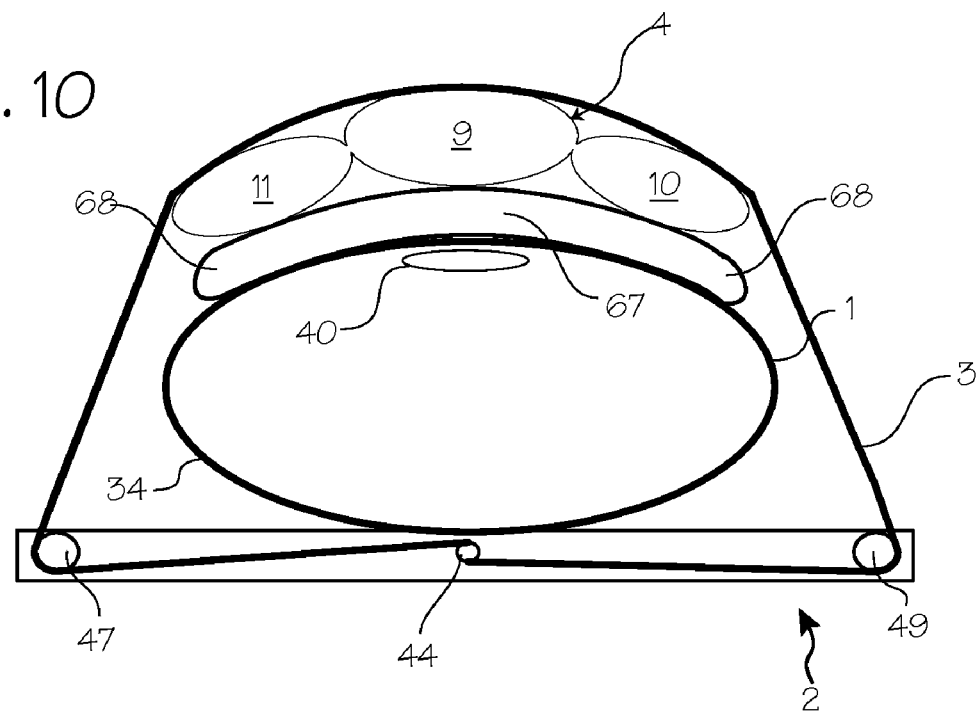
FIG. 10 illustrates a patient in an automatic chest compression device, a first bladder disposed above the sternum, and a second bladder disposed below the first bladder.

FIG. 10 illustrates a patient 1 in an automatic chest compression device 2, a first bladder 4 disposed above the sternum 40, and a second bladder 67 disposed below the bladder. In this orientation, the second bladder helps to more evenly distribute the force of compressions along the patient's thorax 34, although preferential displacement of the sternum may still take place during compressions.

Figure 11:
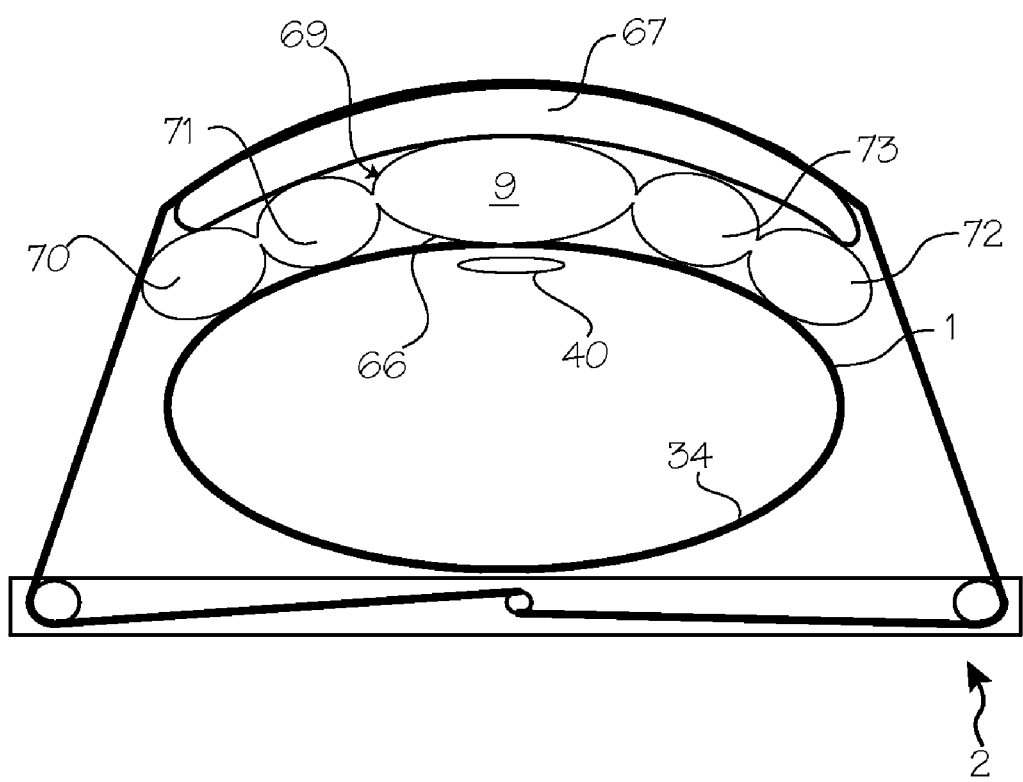
FIG. 11 illustrates a patient in an automatic chest compression device, a five-sectioned bladder disposed above the sternum, and a second bladder disposed above the five-sectioned bladder.

FIG. 11 illustrates a patient 1 in an automatic chest compression device 2, a five-sectioned bladder 69 disposed above the sternum 40, and a second bladder 67 disposed above the five-sectioned bladder. The five-sectioned bladder allows fluid communication between the left lateral section 70, left medial section 71, right lateral section 72, right medial section 73, and the central section 9. Thus, when under a load the fluid pressure will transfer from the lateral and medial sections to the central section. This results in preferential displacement of the sternum 40 as the central section 9 preferentially expands.

The five-sectioned bladder 69 is made of similar materials and filled with similar liquids or foams as the bladder 4. In addition, the central section 9 of the five sectioned bladder may be constructed with either an elastic or a pleated bottom surface 66. In general, a bladder may have any number of sections. However, for most applications a bladder with three sections fits the patient well and also preferentially compresses the patient's sternum during compressions.

Figure 12:
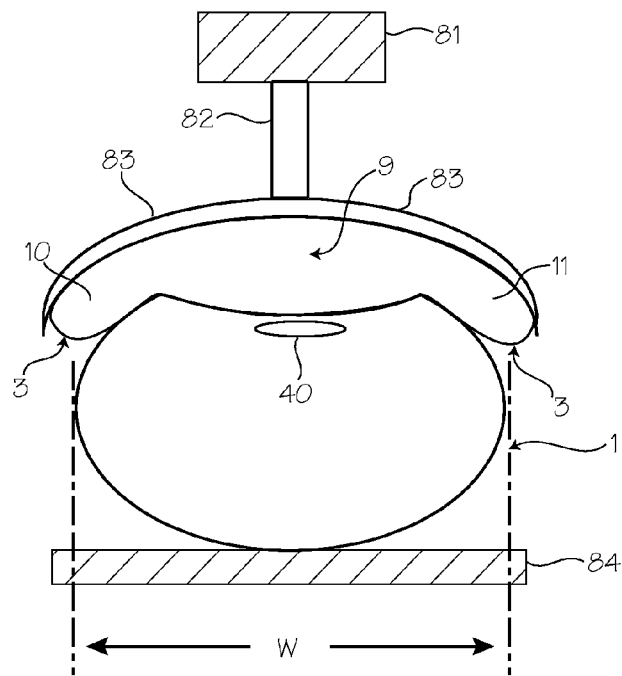
FIG. 12 illustrates a patient receiving chest compressions from a chest compression device in conjunction with a bladder.

FIG. 12 illustrates a patient 1 receiving chest compressions from a chest compression device in conjunction with a bladder 4. An actuator 81 (or other means for providing force) drives a piston 82, and the piston drives a compression plate 83 towards a back plate 84 or other rigid surface. The compression plate compresses the chest as it is repeatedly forced downward on the chest. The plate is sized and dimensioned to cover substantially the entire anterior surface of the chest. A bladder 4 is disposed between the compression plate 83 and the patient's chest. The bladder shown in FIG. 12 is single-sectioned (but may be multi-sectioned) and is filled with a pressure-transmitting medium.

As the compression plate is driven towards the patient's chest, the bladder 4 deforms. Because the sternum 40 is easier to compress than the lateral and medial portions of the patient's chest, the bladder's lateral portions, 10 and 11, are compressed more than the bladder's central portion 9. Thus, pressure is transmitted to the central section 9, which in turn causes the central portion of the bladder to expand. The expansion of the central portion of the bladder causes the chest to be compressed posteriorly in the location of the sternum 40. This effect occurs in both single-sectioned and multi-sectioned bladders.

Figure 13:
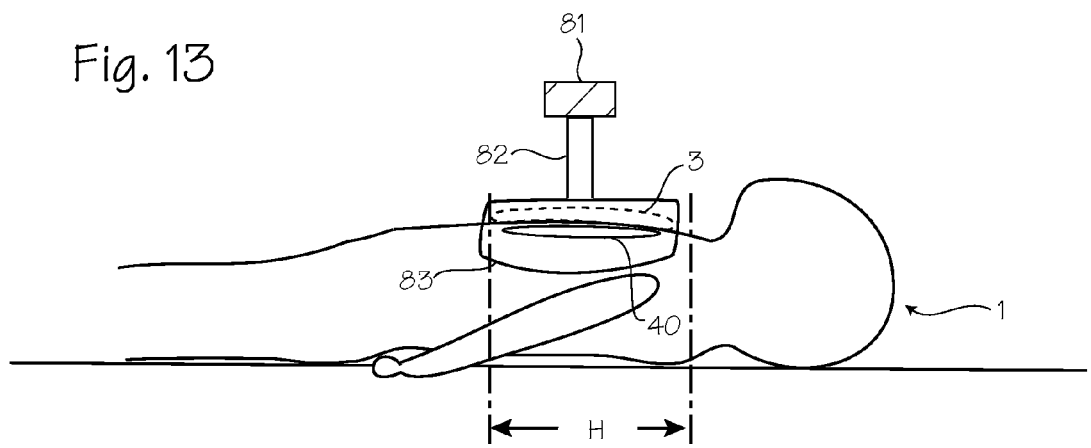
FIG. 13 is a side view of the patient, bladder, actuator, piston, and compression plate shown in FIG. 12.

FIG. 13 is a side view of the patient 1, bladder 4, actuator 81, piston 82, and compression plate 83 shown in FIG. 12. The bladder may be sized and proportioned to occupy the entire area of the bottom of the compression plate 83. Thus, the bladder may span substantially the entire breadth W (shown in FIG. 12) and height H (shown in FIG. 13) of the patient's chest. The bladder may be smaller, though the bladder is still large enough to cause preferential displacement of the sternum 40 as the bladder deforms during compressions.

Figure 14:
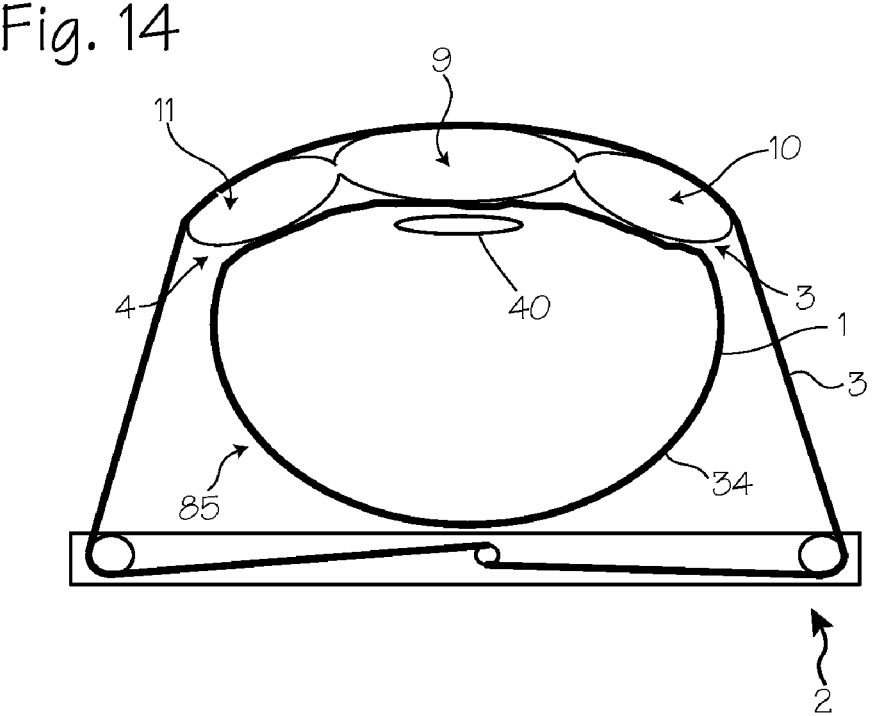
FIG. 14 illustrates a barrel-chested patient receiving chest compressions from a chest compression device in conjunction with a bladder.

FIG. 14 illustrates the effect of the compression device on a barrel-chested patient 85. The chest compression device performs compressions by repeatedly tightening and loosening a belt 3 disposed over the patient's chest, and is shown in FIG. 14 in its compression state. The bladder 4 is disposed between the belt 3 and the patient's sternum 40. In most patients, the bladder will cause the patient's sternum to be compressed preferentially. However, with barrel-chested patients, the sternum is less compliant, and offers more resistance to compression than the sternum of the typical patient. When the chest compression device is applied and operated on a barrel-chested patient, the bladder's right lateral section 10, left lateral section 11, and central section 9 tend to compress more evenly, as shown in FIG. 14. Nevertheless, CPR remains effective and the bladder continues to re-distribute the pressure of compressions. Thus, more total force can be applied to the patient's chest without significantly increasing the risk of injury to the patient.

Figure 15:
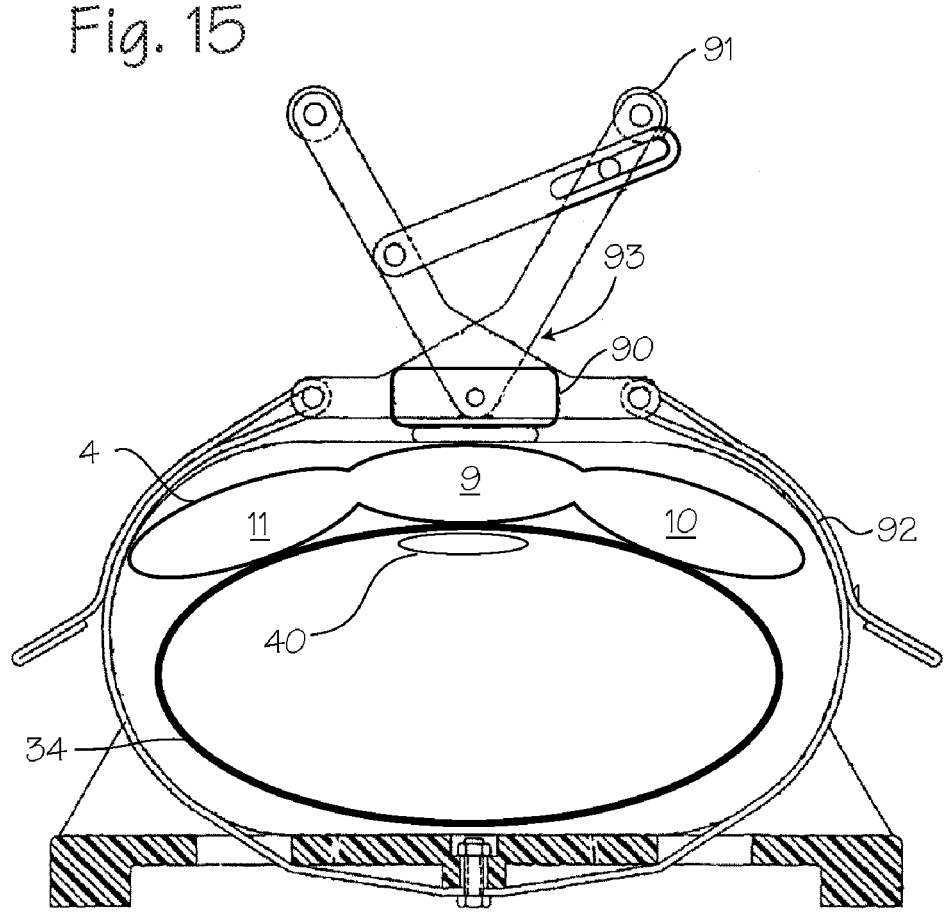
FIG. 15 illustrates a patient receiving chest compressions from a chest compression device in conjunction with a bladder.

A variety of other CPR devices may also be used in conjunction with the bladder. A belt or band may be disposed around the patient's chest and various other means for tightening the belt (such as a manual pull-lever, scissors-like device, or motor) be operably attached to the belt. As illustrated in FIG. 15, the device shown in Kelly (U.S. Pat. No. 5,738,637), for instance, includes a base 90 adapted for placement over the central region of a patient's chest, coupled to an actuator 91 which is connected to a belt 92 configured to wrap around the patient's chest 34 and a "force converter" 93 mounted on the base and coupled to the actuator and the belt. The force converter converts forces applied downwardly on the actuator into tangential forces applied to the belt. The bladder 4 described above can be interposed between the base described in Kelly and the patient's thorax 34 to further refine the application of force to the patient.

In other devices the means for compressing the chest may comprise a piston, a plate, or other means for applying force to the chest operably connected to a means for driving the piston, plate, or other means for applying force, such as the Thumper™ device. The means for driving the piston, plate, or other means for applying force may comprise a motor, manual pull-lever, an actuator, or other means for driving a means for applying force to the patient's chest. The bladder may also be used in conjunction with manual chest compressions when compressions are performed with a rigid compression surface, such as a compression board. In any case, the bladder may be provided between the compressing device and the patient's chest and, in use, performs similarly to the devices shown in FIGS. 1, 5 and 6. In another device the bladder may be disposed between a compression vest and the patient's chest. The bladder may be used with any chest compression technique that uses a means for applying a force to the chest of the patient.

The bladder may also comprise many forms. The bladder 4 may be single sectioned or may be multi-sectioned. The bladder 4 may be of various sizes with a volume of up to several hundred cubic centimeters. The entire bladder 4 may be about 3 to about 18 inches high (relative to the patient, as defined by superior-inferior axis 12), about 4 to about 24 inches wide (relative to the patient, as defined by lateral-medial axis 13), and about ¼ inch to about 3 inches thick. The bladder 4 may assume a variety of shapes in addition to the rectangular bladder shown, including a cylinder, or other geometrical shape having a thickness smaller than the bladder's width and length. Thus, the bladder may be provided in a variety of sizes to match the chest size of different patients, such as men, women, very small individuals, or very large individuals.

The bladder 4 may comprise an inelastic material such as double-coated urethane over a high strength fabric, including polyester, Kevlar®, or a 200 Denier Nylon Oxford fabric. Other materials of similar strength and inelasticity may be used, and the bladder may be formed of separate pieces as shown in FIG. 2, or it may be formed by injection molding or other processes. The material may be slightly elastic, and may stretch about 20% when in use. The modulus of the material may be greater than about 2000 psi. However, the bladder itself is designed such that the central bladder section 9 expands when the lateral sections 10, and 11, are compressed. The bladder may be only partially filled with foam, foam combined with air, or some other pressure-transmitting medium. In this case, the central section may still expand when the lateral sections are compressed. Though the lateral sections may beneficially be compressed and deformed to the extent that they are completely emptied during compressions, the central section should not be so elastic or deformable that it is completely flattened (so that the upper and lower sheets meet) during compressions.

Suitable foams for use with the bladder include SIF® foam, polyurethane, polyethylene, or other polymer foams. The foam may be from about 5 pores per inch to greater than 100 pores per inch, though about 15 pores per inch is sufficient for most applications. The bladder 4 may filled with air, foam, water, gel, hydrogel, alcohol, oil or any other fluid that can communicate pressure from the right lateral section 10 and the left lateral section 11 to the central section 9 of the bladder. If filled with a liquid, the liquid may have a low viscosity to allow for easier transfer of the liquid between bladder sections. The liquid may also be light (of a low molecular weight) to lower the weight of the bladder. The bladder may also be provided with ribs made from plastic, or other flexible material, to provide the bladder with a skeletal frame. The skeletal frame may be used alone or in combination with the foam to enhance the resilient expansion of the bladder during relaxation of the chest compression device.

The bladder may be coated, on either the inner surfaces, outer surfaces, or both, to make it water resistant, water proof, or to make it easier to join sections of the bladder together (when forming multi-sectioned bladders). Whatever the material or coating, the bladder should be resistant to water and bodily fluids and maintain its material properties both wet and dry. Desirable coatings include polyurethane, polyester coated with polyurethane, polyether polyurethane, or similar materials. The thickness of the coating may vary, but is about 0.003 inches to about 0.050 inches; however, a thickness of about 0.006 inches is suitable for most bladder products.

The bladder may be provided with additional features if desired. For example, the bladder may be provided with markings or compartments to assist the rescuer in placing the bladder properly on the patient's chest. The bladder may be provided with a transducer, pressure sensor, or force sensor. The sensor may measure the force applied to the bladder or the pressure inside the bladder.

As mentioned above, the bladder may be provided with a valve which permits air to flow in and out of the bladder only when atmospheric pressure is about equal to the pressure in the bladder. In general, the valve leaks when there is a small differential pressure across the valve. That is, when the bladder pressure slightly exceeds ambient pressure the valve will allow pressure equalization. However, when the bladder pressure rises sharply (during compressions) the valve competently closes to prevent flow past the valve and out of the bladder. Thus, the valve performs as a leaky check valve that permits leakage when there is a small differential pressure across the valve but seals tightly when there is a large differential pressure across the valve. We refer to such valves as equalizing check valves.

The valve allows the bladder to be stored in an uninflated state (such as when it is folded for packaging or transport) and yet achieve atmospheric pressure before the bladder is readied for use, and it allows the bladder to be manufactured and filled in one place and shipped to its location of use without taking any action to adjust the pressure in the bladder. Additionally, the valve permits consistent operation of the device in scenarios in which ambient pressure may change rapidly, such as during helicopter transport, use on aircraft, or use in mountainous areas.

The valve may comprise any suitable valve that allows air to flow only when atmospheric pressure is about equal to the pressure in the bladder. A simple example would be a floppy latex tube inside of the bladder in fluid communication with an aperture in the bladder opening to the outside. In more complicated constructions, the valve may comprise a top layer and a bottom layer, where at least the bottom layer is made of a resilient material. The top layer and bottom layer are sealed together while leaving least one relief conduit provided between the layers and a hole provided in the top layer. The top layer is disposed so that the hole opens to the atmosphere and the bottom layer is disposed so that the conduit opens inside the bladder. When atmospheric pressure is about equal to the pressure in the bladder then air flows back and forth through the hole, through the relief conduits, and through the bladder. When pressure is applied to the bladder, the pressure in the bladder forces the layers together, causing the relief conduit to collapse and thus seal the bladder. A suitable valve of this type is described in Pekar, Inlet Check Valve for Pump Mechanism, U.S. Pat. No. 5,372,487.

Another suitable valve is a membrane valve, wherein each membrane has a small hole that lines up with the other small hole unless the valve experiences a large increase in pressure. When a compression begins the holes no longer line up, thus sealing the bladder for the duration of the compression. Other means for maintaining the total amount of air within the bladder while the bladder is compressed is a peel-off tab that is used to seal the bladder just before compressions, a classic check valve which is lightly spring biased to remain open, a check valve that plugs during the first compression, or a ball check valve with a ball in a tube that seals with the closure of a belt used to compress the chest. Other valve examples include a plunger held down by Velcro™ (or other releasably attached securing means) or other valves that close at the beginning of compressions.

The bladder may be provided with other features, including a liner or a cover that covers and protects the bladder and allows the bladder to be re-used. The liner may be designed for use as part of a belt or other compression means, or the liner may merely cover the bladder without additional features. (Thus, the pad and liner may be easily attached to a means for compressing the chest). The liner may comprise a low friction, water-resistant, non-resilient material such as PTFE, ePTFE (both are Teflon®), or similar materials. The liner may cover one or more surfaces of the bladder, part of a bladder surface, or the entire bladder. In addition, one or more surfaces of the bladder may be coated with or made of PTFE, ePTFE (both are Teflon®), or similar materials.

The bladder may also be provided with an integrated defibrillation device, with ECG and defibrillation electrodes, and/or other electrodes to measure impedance. The ECG and defibrillation electrodes (which may be the same electrodes as the impedance measurement electrodes) may be breakaway electrodes that break off the surface of the pad when the pad is removed from the patient. The electrodes then remain on the patient's chest for continued use in monitoring the patient. The bladder may also be provided with one or more means for measuring biological feedback parameters of interest to medical personnel, including blood pressure monitors, patient temperature, blood oxygen levels, or other biological parameters. In addition, the bladder may be designed to be used repeatedly on different patients, or may be designed to be disposable with each rescue.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A system for performing CPR on a patient, said system comprising:

a chest compression means comprising a belt adapted to be disposed at least partially about the chest of the patient and a means for repetitively tightening the belt at a resuscitative rate, said means operably connected to the belt;

a bladder disposed between the chest compression means and the chest of the patient, and at least two dividers disposed within the bladder, such that the bladder is divided to form a left lateral section in fluid communication with a central section and a right lateral section in fluid communication with said central section, and wherein each section contains a pressure-transmitting medium, and the bladder is disposed relative to the belt during use between the belt and the chest of the patient and the central section is disposed over the sternum of the patient.

2. The system of claim 1 wherein the bladder is filled with an open-celled foam.

3. The system of claim 2 further comprising a defibrillator operably connected to the patient.

4. The system of claim 2 further comprising a means for measuring biological parameters operably connected to the patient.

5. The system of claim 2 wherein the bladder further comprises an aperture communicating from the interior of the bladder to the exterior of the bladder, and a valve controlling the aperture, wherein the valve is open when atmospheric pressure is about equal to the pressure inside the bladder and wherein the valve closes during a compression.

6. The system of claim 2 further comprising:
a defibrillator operably connected to the patient;
a means for measuring biological parameters operably connected to the patient;
an aperture in the bladder, and a valve controlling flow through the aperture, wherein the valve is open when atmospheric pressure is about equal to the pressure inside the bladder and wherein the valve closes during a compression.

7. The bladder of claim 1 wherein the bottom surface of the central section is made of an elastic material.

8. The bladder of claim 5 wherein the bottom surface of the central section is made of an elastic material.

9. The bladder of claim 6 wherein the bottom surface of the central section is made of an elastic material.

10. The bladder of claim 1 wherein the bottom surface of the central section is pleated.

11. The bladder of claim 10 wherein the bottom surface of the central section is comprised of an elastic material.

12. The device of claim 1, wherein the bladder further comprises a first fluid pathway connecting the left lateral section and the central section and a second fluid pathway connecting the right lateral section and the central section.

13. A device for compressing the chest of a patient comprising:
a base adapted for placement over the central region of a patient's chest;
an actuator connected to a belt configured to wrap around the patient's chest;
a force converter mounted on the base and coupled to the actuator and the belt, said force converter operable to convert forces applied downwardly on the actuator into tangential forces applied to the belt; and
a fluid-filled bladder disposed between the base and the patient's chest, and at least two dividers disposed within the bladder, such that the bladder is divided to form a left lateral section in fluid communication with a central section and a right lateral section in fluid communication with said central section.

14. The device of claim 13 wherein the bladder comprises:
a right lateral section adapted to be disposed over the right side of the patient's chest, a center section adapted to be disposed over the center of the patient's chest, and a left lateral section adapted to be disposed over the left side of the patients chest, and the bladder having a first relaxed configuration which it assumes when the belt is loosened about the chest and a second pressurized configuration which it assumes when the belt is constricted about the chest of the patient;
wherein in said relaxed configuration the right lateral section, center section and left lateral section are each filled with fluid and in said pressurized configuration the right lateral section and left lateral section are substantially compressed and the fluid therein is forced into the center section.

15. The device of claim 13, wherein the bladder further comprises:
a resilient foam substantially filling the bladder.

16. The device of claim 14, wherein the bladder further comprises:
a resilient foam substantially filling the bladder.

17. The device of claim 13, wherein the bladder spans substantially the entire breadth of the patient's chest.

18. The device of claim 13, wherein the bladder spans substantially the entire breadth and height of the patient's chest.

19. The device of claim 13, wherein the bladder is about 16 inches wide and 8 inches high, relative to the patient.

20. The device of claim 14, wherein the bladder spans substantially the entire breadth of the patient's chest.

21. The device of claim 14, wherein the bladder spans substantially the entire breadth and height of the patient's chest.

22. The device of claim 14, wherein the bladder is about 16 inches wide and 8 inches high, relative to the patient.

23. A system for performing CPR on a patient, said system comprising:
a chest compression means comprising a belt adapted to be disposed at least partially about the chest of the patient and a means for repetitively tightening the belt at a resuscitative rate, said means operably connected to the belt;
a bladder disposed between the chest compression means and the chest of the patient, and at least two dividers disposed within the bladder, such that the bladder is divided to form a left lateral section in fluid communication with a central section and a right lateral section in fluid communication with said central section, and wherein each section contains a pressure-transmitting medium, and the bladder is disposed relative to the belt during use between the belt and the chest of the patient and the central section is disposed over the sternum of the patient;
wherein the pressure-transmitting medium comprises an open-celled foam;
wherein the bladder further comprises an aperture communicating from the interior of the bladder to the exterior of the bladder, and a valve controlling the aperture, wherein the valve is open when atmospheric pressure is about equal to the pressure inside the bladder and wherein the valve closes during a compression.

24. The system of claim 23 further comprising:
a defibrillator operably connected to the patient;
a means for measuring biological parameters operably connected to the patient.

25. The bladder of claim 23 wherein the bottom surface of the central section is made of an elastic material.

26. The bladder of claim 24 wherein the bottom surface of the central section is made of an elastic material.

27. The system of claim 23 wherein the bladder is filled with an open-celled foam.

* * * * *